US011333873B2

(12) United States Patent
Themelis (10) Patent No.: US 11,333,873 B2
(45) Date of Patent: May 17, 2022

(54) SURGICAL MICROSCOPE WITH MOVABLE BEAM DEFLECTOR, METHOD FOR OPERATING THE SAME AND RETROFIT-KIT (71) Applicant: LEICA INSTRUMENTS (SINGAPORE) PTE. LTD., Singapore (SG)

(72) Inventor: George Themelis, Lindau (DE)

(73) Assignee: LEICA INSTRUMENTS (SINGAPORE) PTE. LTD., Singapore (SG)

(*) Notice: Subject to any disclaimer, the term of this patent is extended or adjusted under 35 U.S.C. 154(b) by 514 days.

(21) Appl. No.: 16/274,315

(22) Filed: Feb. 13, 2019

(65) Prior Publication Data

US 2019/0265453 A1 Aug. 29, 2019

(30) Foreign Application Priority Data

Feb. 23, 2018 (EP) ..................... 18158423

(51) Int. Cl.
G02B 21/06 (2006.01)
G02B 21/00 (2006.01)
(Continued)

(52) U.S. Cl.
CPC .............. G02B 21/06 (2013.01); A61B 90/20 (2016.02); A61B 90/25 (2016.02); A61B 90/30 (2016.02);
(Continued)

(58) Field of Classification Search
CPC .......... A61B 90/25; A61B 90/00; A61B 90/20; A61B 90/361; A61B 90/37; A61B 90/50; A61B 2090/367; A61B 2090/371; A61B 2090/373; A61B 2090/368; A61B 2090/3618; A61B 2017/00123; A61B 34/30; H04N 5/247; H04N 5/23299;
(Continued)

(56) References Cited

U.S. PATENT DOCUMENTS

2008/0212171 A1 9/2008 Strahle et al.
2008/0266657 A1 10/2008 Strahle et al.
(Continued)

FOREIGN PATENT DOCUMENTS

JP S57-102607 A 6/1982
WO WO-2007101695 A1 * 9/2007 ......... G02B 26/0816

Primary Examiner — Darryl J Collins
Assistant Examiner — Tamara Y. Washington
(74) Attorney, Agent, or Firm — Hodgson Russ LLP (57) ABSTRACT A surgical microscope, a method for observing an object in an observation area during surgery, and a retrofit-kit for a surgical microscope are provided. The surgical microscope includes at least one optical carrier for variably deflecting an observation axis of an optical observation assembly into an optical viewing axis directed towards the observation area. The optical carrier includes at least one optical beam deflector and is arranged between the optical observation assembly and the observation area. The optical carrier further includes a movable range-setting system for supporting the at least one optical beam deflector and for positioning the at least one optical beam deflector at a variable distance from the optical observation assembly.

14 Claims, 4 Drawing Sheets (51) Int. Cl.
  *A61B 90/25* (2016.01)
  *A61B 90/30* (2016.01)
  *A61B 90/20* (2016.01)
  *G02B 26/10* (2006.01)

(52) U.S. Cl.
  CPC ......... *G02B 21/002* (2013.01); *G02B 26/101* (2013.01); *G02B 26/105* (2013.01); *G02B 21/0012* (2013.01)

(58) Field of Classification Search
  CPC .. H04N 13/204; G06F 3/013; G02B 26/0816; G02B 21/368; G02B 21/0012; G02B 21/24; G02B 21/06
  See application file for complete search history.

(56) References Cited

U.S. PATENT DOCUMENTS

| | | |
|---|---|---|
| 2009/0059363 A1 | 3/2009 | Straehle et al. |
| 2010/0097692 A1 | 4/2010 | Glaser et al. |
| 2013/0083289 A1 | 4/2013 | Hauger et al. |
| 2020/0033575 A1* | 1/2020 | Mueller ............... G02B 25/001 |

* cited by examiner

SURGICAL MICROSCOPE WITH MOVABLE BEAM DEFLECTOR, METHOD FOR OPERATING THE SAME AND RETROFIT-KIT

CROSS REFERENCE TO RELATED APPLICATIONS

This application claims priority of European patent application number 18158423.6 filed Feb. 23, 2018, the entire disclosure of which is incorporated by reference herein.

FIELD OF THE INVENTION

The invention relates to a surgical microscope for observing an object in an observation area during surgery. The invention further relates to a method for observing an object in an observation area during surgery and to a retrofit-kit.

BACKGROUND OF THE INVENTION

Surgical microscopes of the art are known but have several disadvantages. Changing a direction of observation is, for example, difficult as such a change in the direction of observation, e.g. by rotating an optical carrier of the surgical microscope, also moves an optical eyepiece. Movement of the latter makes it difficult to keep the eyes (of the observer, e.g. a surgeon) aligned.

Further solutions of the art apply a robotic arm which is controlled by a computer in order to set the position and rotation of the optics carrier. Such a robotic arm-based system, however, may require preoperative planning and the robotic arm is expensive, bulky, takes up valuable operation space in an operating room and its potential is not even close to being fully exploited.

SUMMARY OF THE INVENTION

An object of the present invention is therefore to provide a surgical microscope, a method and a retrofit-kit which allow an uninterrupted surgical workflow when the direction of observation is changed, and which is less costly and less bulky than a robotic arm.

The inventive surgical microscope mentioned in the beginning solves this object by at least one optical carrier for variably deflecting an observation axis of an optical observation assembly into an optical viewing axis directed towards the observation area, wherein the optical carrier comprises at least one optical beam deflector and is arranged between the optical observation assembly and the observation area.

The inventive method mentioned in the beginning solves the above object by comprising the steps of: variably deflecting an observation axis of an optical observation assembly into an optical viewing axis directed towards the observation area; and propagating light stemming from the observation area essentially along the optical viewing axis and the observation axis and imaging said light via an optical observation assembly.

The inventive retrofit-kit mentioned in the beginning solves the above objects by comprising at least one coupling with at least one optical beam deflector, an optical input axis which is variably deflected into an optical output axis by the at least one optical beam deflector, wherein the coupling is adapted to be mounted to a surgical microscope, such that the optical input axis corresponds to the observation axis of an optical observation assembly.

The inventive surgical microscope, the inventive method and the inventive retrofit-kit thus have the advantages that they are lighter, less expensive and less bulky than solutions of the art. The inventive surgical microscope and/or the inventive retrofit-kit may therefore be suitably applied in an existing operative or surgical environment. Furthermore, the inventive surgical microscope, the retrofit-kit and the method allow for easy adjustment or change of the optical viewing axis without the need to position heavy and/or sensitive elements, such as the robotic arm. Consequently, the field of view is adjusted very rapidly. Preferably, the eyepiece as well as the surgeon's eyes may remain at a fixed position even during tilt and/or rotation of the optical viewing axis. The inventive surgical microscope is thus more compact than the solutions disclosed in the art, e.g. surgical microscopes with a robotic arm.

The inventive surgical microscope, method and retrofit-kit may be improved by specific embodiments which will be described in the following. Technical features of the embodiments may be arbitrarily combined with each other or omitted if the technical effect obtained by the omitted technical feature(s) is not relevant to the present invention.

The coupling is to be understood as a support structure which may be attached to a surgical microscope. Apart from the at least one optical beam deflector which may be attached to and supported by the optical carrier, any arbitrary number of optical elements like mirrors, lenses, prisms, refractive or catadioptric elements may be provided and supported by the optical carrier. The retrofit-kit may comprise a further optical carrier for supporting optical elements. The observation axis is determined by the optical observation assembly and in general corresponds to the optical axis of said assembly.

The variable deflection of the observation axis into the optical viewing axis may be performed using at least one reflective element as a mirror, a refractive element like a prism (which may additionally provide a reflection, e.g. via total internal reflection) or a catadioptric element combining both. The above listed optical elements represent specific embodiments of the at least one optical beam deflector.

The surgical microscope therefore may comprise an optical path, wherein light from the observation area propagating along the optical path from the observation area towards the optical carrier is deflected at or by the at least one optical beam deflector and consequently propagates through the optical observation assembly for imaging or observing.

In another embodiment of the inventive surgical microscope the at least one optical beam deflector is movable with respect to the optical observation assembly with regard to at least one of tilt and distance. In the corresponding embodiment of the method, the optical beam deflector moves with respect to the optical observation assembly, in particular tilts or translates such that a tilt and/or distance between the at least one optical beam deflector and the optical observation assembly is modified.

This has the advantage that an observation angle, i.e. the angle at which the optical viewing axis is oriented with respect to the observation area, may be freely selected.

Furthermore, the footprint, costs and complexity of the surgical microscope and the inventive method may be reduced. A viewing direction and viewing angle provided by the surgical microscope may be rapidly adjusted as the at least one movable optical beam deflector has a reduced inertia of the moving parts (as compared to a robotic arm). Such a deflection mechanism may furthermore be much more compact than a robotic arm.

In another embodiment of the inventive surgical microscope the optical carrier may comprise a pair of optical beam deflectors, of which at least one is tiltable and/or moveable with respect to the other. In the corresponding inventive method, at least one optical beam deflector of the pair of optical beam deflectors deflects the observation axis.

This has the advantage that the possible variation of the observation angle, as well as the position of the optical viewing axis may be further increased. Additionally, a more complex optical path may be possible, e.g. if an incident angle on at least one optical beam deflector is limited (also limiting an angle of deflection) but a larger angle of deflection is desired.

Either one or both optical beam deflectors of the pair may be tiltable and/or movable, wherein preferably both optical beam deflectors are at least tiltable. Also, both beam deflectors may be movable with respect to each other. A movement is to be understood to comprise a tilt, rotation and linear translation, i.e. a general change of spatial position and/or orientation.

The movement of the at least one optical beam deflector of the pair, in particular the linear translation of said beam deflector is preferably performed along the optical path, such that changing the distance between the at least one optical beam deflector and the optical observation assembly or the distance between both optical beam deflectors (of the pair) does not require readjusting the tilt of the at least one optical beam deflector. Furthermore, the optical path preferably corresponds to the observation axis and the optical viewing axis, which may be approximately centered on optical components as, for instance, the at least one optical beam deflector.

In another embodiment of the invention, more than two optical beam deflectors may be provided. Such an embodiment allows for more complex optical paths as well as for dividing a desired deflection of the optical path on two optical beam deflectors. The latter may have a limited angular range within which a deflection is possible (cp. the maximum glancing angle if total internal reflection is applied).

In another embodiment of the inventive surgical microscope a drive system for moving and/or tilting of the at least one optical beam deflector may be provided. The corresponding inventive method therefore moves and/or tilts the at least one optical beam deflector using a drive system.

Such a drive system has the advantage that the variable deflection of the observation axis may be automated, to allow an observer, e.g. the surgeon, to easily adjust the optical viewing axis of the surgical microscope by means of control interface means as, for instance, buttons, a joystick or the like.

The drive system may comprise linear translation stages and/or rotational or tilt stages which allow for precise and repeatable adjustment of the optical viewing axis.

In another embodiment of the inventive surgical microscope, a controller module may be provided, wherein said controller module may have at least one control data input terminal for inputting control data and at least one driving data output terminal connected to the drive system for providing driving data to the drive system. The controller module therefore transcribes or translates control data which are input into output driving data and provides such data to the drive system. The controller module controls the drive system. This may be performed using open loop or closed loop controlling performed by a corresponding open loop circuit or closed loop circuit comprised in the controller module. The control data may be manually input, e.g. by pressing a button or by a variation of a suitable physical property which is manually changed by the observer, e.g. the surgeon. One simple example of manually input control data is the variable resistance of a potentiometer set by the surgeon. The resistance may correspond to a tilt of the at least one optical beam deflector.

The control data may also be provided by a computer, i.e. in the form of a digital signal.

In a further embodiment of the inventive surgical microscope or inventive method, the optical carrier may comprise a rotational support assembly for supporting the at least one optical beam deflector, the rotational support assembly being rotatable with respect to the rotational axis. The rotational support assembly may be understood as a supporting structure on which the at least one optical beam deflector, preferably both beam deflectors of the pair of beam deflectors, are attached. The rotational support assembly may be supported by the optical carrier. In a corresponding embodiment of the retrofit-kit, the rotational support assembly may therefore be supported by the further optical carrier.

The at least one optical beam deflector may be rotated around the rotational axis and does not change its relative position with respect to the rotational support assembly during a rotation.

In a further embodiment of the inventive surgical microscope or the corresponding inventive method, the rotational axis coincides with the observation axis of the optical observation assembly. In this embodiment, the optical observation assembly may remain at a fixed position, wherein the at least one optical beam deflector, preferably the pair of optical beam deflectors, are rotated by means of the rotational support assembly.

This embodiment has the advantage that a rotation of the rotational support assembly only modifies an angle between the optical observation assembly and the rotational support assembly and does not require realigning optical elements, e.g. the at least one optical beam deflector of the rotational support assembly with respect to the observation axis. In other words, the observation axis may remain (preferably centered) on the at least one optical beam deflector.

A rotation of the at least one optical beam deflector allows the surgeon to change a viewing perspective. The change of perspective may mimic a movement of the surgical microscope to one side combined with a simultaneous tilt of its observation axis in order to remain pointed at the observation area. However, according to the invention, the optical observation assembly remains fixed and the perspective is changed merely by adjusting the at least one optical beam deflector.

In the previously described embodiments as well in the embodiments which will be described in the following, it is particularly advantageous if a variable deflection of the observation axis into the optical viewing axis does not change further optical properties of the surgical microscope. Exemplarily, adjusting the deflection may maintain the length of the optical path and consequently also the setting of the focal position of the surgical microscope.

However, in further embodiments of the inventive surgical microscope, a focus readjustment module may be provided which detects a change in the optical path length and adapts the focusing of optical elements of the surgical microscope. Here, as an example, an electrically tunable lens may be applied to readjust the focus (i.e. to change the set focal distance) of the surgical microscope.

In another embodiment of the inventive surgical microscope or retrofit-kit the optical carrier or the further optical carrier, respectively, comprises a movable range-setting support system for supporting the at least one optical beam deflector and for positioning the at least one optical beam deflector at a variable distance from the optical observation assembly. In the corresponding inventive method, a movable range-setting support system supports the at least one optical beam deflector and varies a distance between the at least one optical beam deflector and the optical observation assembly.

This has the advantage that the range of angular positioning of the optical viewing axis with respect to the observation area may be increased.

It may be possible to define an origin of the optical viewing axis at an optical beam deflector, in particular at the beam deflector which is closest to the observation area. The movable range-setting support system changes the position of said origin. The term "origin" is to be understood as one predetermined point through which the optical viewing axis as well as the optical path passes. It is not to be understood as the point from which electromagnetic radiation is emitted. The movable range-setting support system therefore allows the possible tilt of the optical viewing axis to be altered and, additionally, to translate the resulting optical viewing axis parallelly by means of the movement via the movable range-setting support system.

By means of the movable range-setting support system, the distance between the two optical beam deflectors may be varied (if the pair of optical beam deflectors is applied). Preferably, the movement of the range-setting support system occurs along the optical path.

The range-setting support system may, in particular, be supported by the rotational support system. This has the advantage that a rotation of the rotational support system does not misalign the at least one optical beam deflector which is moved by the range-setting support system as the entire range-setting support system may be rotated.

The movable range setting support system may provide a guiding element such as a guiding trail, an elongated guiding recess, a guiding rod or a similar structure. Along said structure, the at least one optical beam deflector may be linearly translated.

Another embodiment of the inventive surgical microscope may comprise a light source arrangement for providing illumination light and/or excitation light to the observation area. The illumination light may be partially reflected or partially transmitted by the object located in the observation area.

Similarly, excitation light may be provided to the observation area, wherein said excitation light may trigger the generation of electromagnetic radiation (e.g. by excitation of fluorescence). Said electromagnetic radiation or illumination light being spatially modified by reflection or transmission at or through the object may be referred to as observation light. The observation light represents spatially resolved physical properties of the object and may propagate along the optical viewing axis, through the optical carrier (and eventually through the further optical carrier if a retrofit-kit is applied) and is in particular deflected by the at least one optical beam deflector and subsequently propagates to or into the optical observation assembly for observation.

The light source arrangement may comprise one or more light sources, one or more optical components like optical fibers, lenses, mirrors and the like. Specific light sources may be applied, which may be continuous light sources or pulsed light sources. Moreover, the light sources may emit light in a wavelength range which is not visible to the human eye.

Furthermore, coupling means may be provided for coupling light of the at least one light source into the surgical microscope. This may, for example, be realized by an optical beam combiner or a dichroic mirror.

Coupling light of the at least one light source into the surgical microscope is to be understood as the process of obtaining a propagation of the illumination light and/or the excitation light at least in portions essentially coaxial to the optical viewing axis.

In a further embodiment of the inventive surgical microscope, the range-setting support system comprises a through-hole for providing access to the at least one optical beam deflector from the observation area. Said through-hole may be round or slotted and may additionally be embodied as a guiding recess or a guiding slotted hole applied as a pass-through opening for the optical path. Such a through-hole allows for a compact setup of the surgical microscope and for further miniaturization.

In a further advantageous embodiment of the inventive surgical microscope or inventive method, the range-setting support system is a radial range-setting support system which is rotatable around a support system axis, wherein the rotation of the radial range-setting support system may be synchronized with the rotation of the rotational support assembly.

Thus, two rotational movements may be combined in order to change the distance between the at least one optical beam deflector and the optical observation assembly. The synchronization may require an additional rotation of the element, i.e. the optical beam deflector attached at or supported by the radial range-setting support system. Preferably, the at least one (linearly movable) optical beam deflector is positioned off-center with respect to the support system axis.

In particular, if a pair of optical beam deflectors is applied, a first optical beam deflector may be attached to the radial range-setting support system, wherein a second optical beam deflector is not attached to the radial range setting support system. In this setup, the second optical beam deflector is rotated together with the rotational support assembly, whereas the first optical beam deflector is rotated by the rotational support assembly as well but additionally rotated by means of the radial range-setting support system. Thus, it may be required that the first and/or the second optical beam deflector are supported in a rotatable manner. In other words, the first and/or the second optical beam deflector may be rotatable independently on a rotation of the rotational support assembly or the radial range-setting support system. This allows preventing misalignment of the optical path with respect to the optical beam deflectors.

The above described embodiments of the inventive surgical microscope and the corresponding embodiment of the inventive method may be performed using a corresponding embodiment of the retrofit-kit. Such a retrofit-kit thus supplements prior art surgical microscopes such that a surgical microscope according to the invention is obtained.

The inventive surgical microscope may comprise any number of optical beam deflectors and rotational degrees of freedom. Similarly, a tilt of any optical or mechanical component may be possible around one or two axes, linear movement may be possible along all three spatial directions, being preferably orthogonal to each other. The optical observation assembly may comprise any number of optical observation means including a plurality of eyepieces. Embodiments comprising a light source arrangement may comprise any number of light sources and may combine the corresponding output radiation in any arbitrary composition.

In the following, the present invention is described using accompanying figures which show specific embodiments of the inventive surgical microscope and retrofit-kit. The corresponding embodiments of the inventive method are covered by the description of the respective surgical microscope. Purely exemplary embodiments are shown in the figures, wherein specific technical features of the embodiments may be arbitrarily combined with each other or even omitted if the technical effect obtained by the omitted technical features is not relevant to the present invention. Identical technical features and technical features having the same technical effect will be denoted using the same reference numeral. A repetitive description will be omitted, while differences in technical features between two figures will be emphasized.

BRIEF DESCRIPTION OF THE DRAWING VIEWS

The figures show.

DETAILED DESCRIPTION OF THE INVENTION

Figure 1:
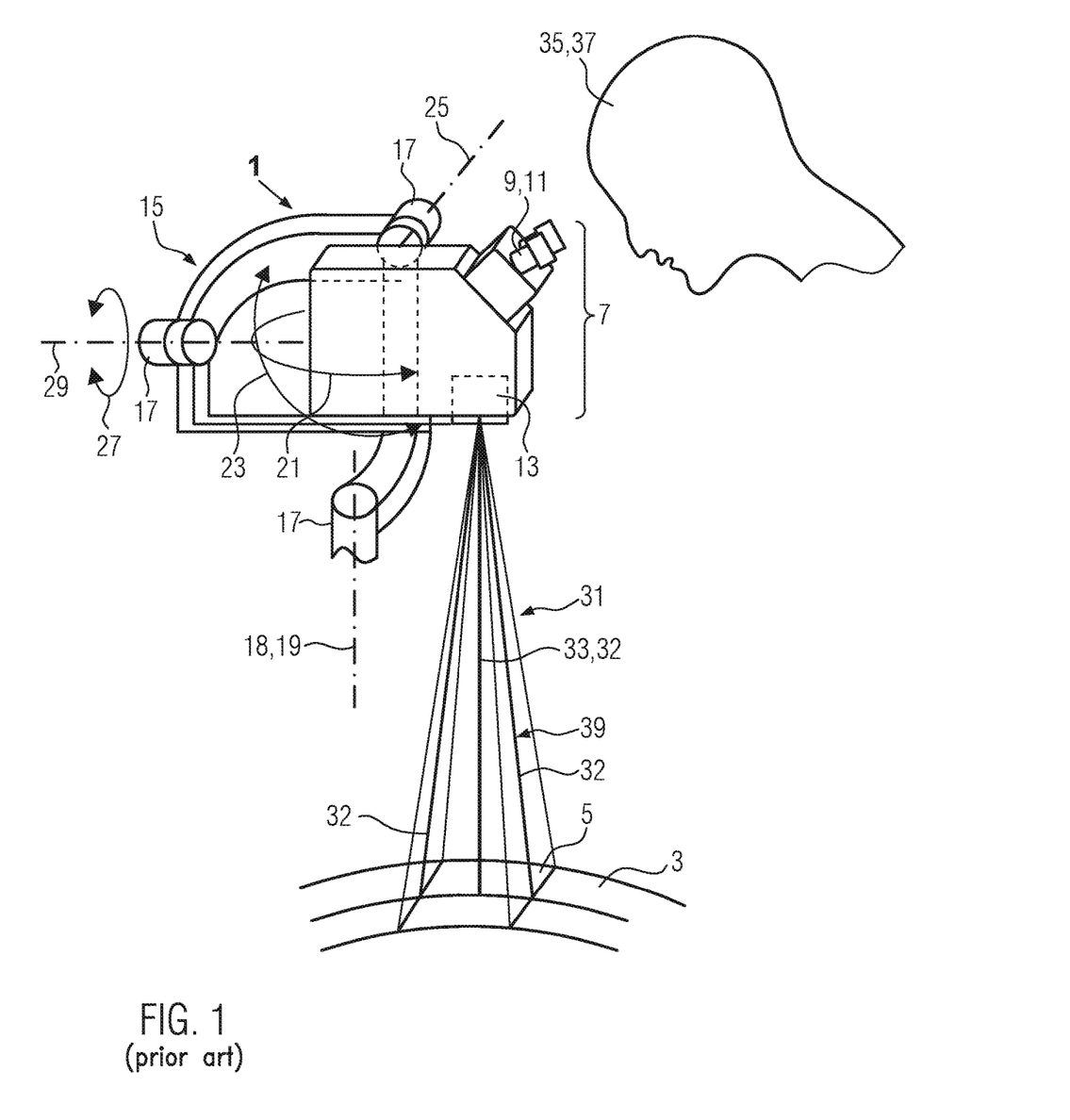
FIG. 1: a surgical microscope of the art.

In FIG. 1 a surgical microscope 1 of the art is shown in a perspective view. The surgical microscope 1 is applied for observing an object 3 in an observation area 5 during a surgery and is shown in a perspective view.

Surgical microscopes 1 of the art comprise an optical observation assembly 7 which comprises an eyepiece 9, also referred to as ocular 11, and an objective assembly 13 which is merely indicated by a dashed line.

The surgical microscope 1 may be mounted on a gimbal mount 15 which comprises three joints 17 in the embodiment shown. The surgical microscope 1 is rotatable about three rotational axes 18. A first rotation 21 is around a vertical axis 19, a second rotation 23 around a first horizontal axis 25 and a third rotation 27 around a second horizontal axis 29. The rotational axes 19, 25, 29 are oriented essentially perpendicular to each other.

The first 21, the second 23 and the third rotation 27 result in a tilt 31 of an observation axis 33 of the optical observation assembly 7. In the figure, three positions 32 of the observation axis 33 are indicated. These rotations 21, 23, 27, however, also result in a tilt 31 of the optical observation assembly 7 and consequently also of the eyepiece 9. A surgeon 35 therefore has to follow the tilt 31 of the optical observation assembly 7 and to change his or her observation position 37. This may interrupt the flow of the surgery.

The observation axis 33 is centered in the observation area 5, wherein the latter is defined by a field of view 39 being a characteristic of the optical observation assembly 7 (which may e.g. be determined by the numerical aperture of optical components (not shown) of the optical observation assembly 7).

It is to be noted that different embodiments of the prior art may comprise only one or two rotational axes 18 and may comprise a mounting system different than the gimbal mount 15 shown in FIG. 1.

Figure 2:
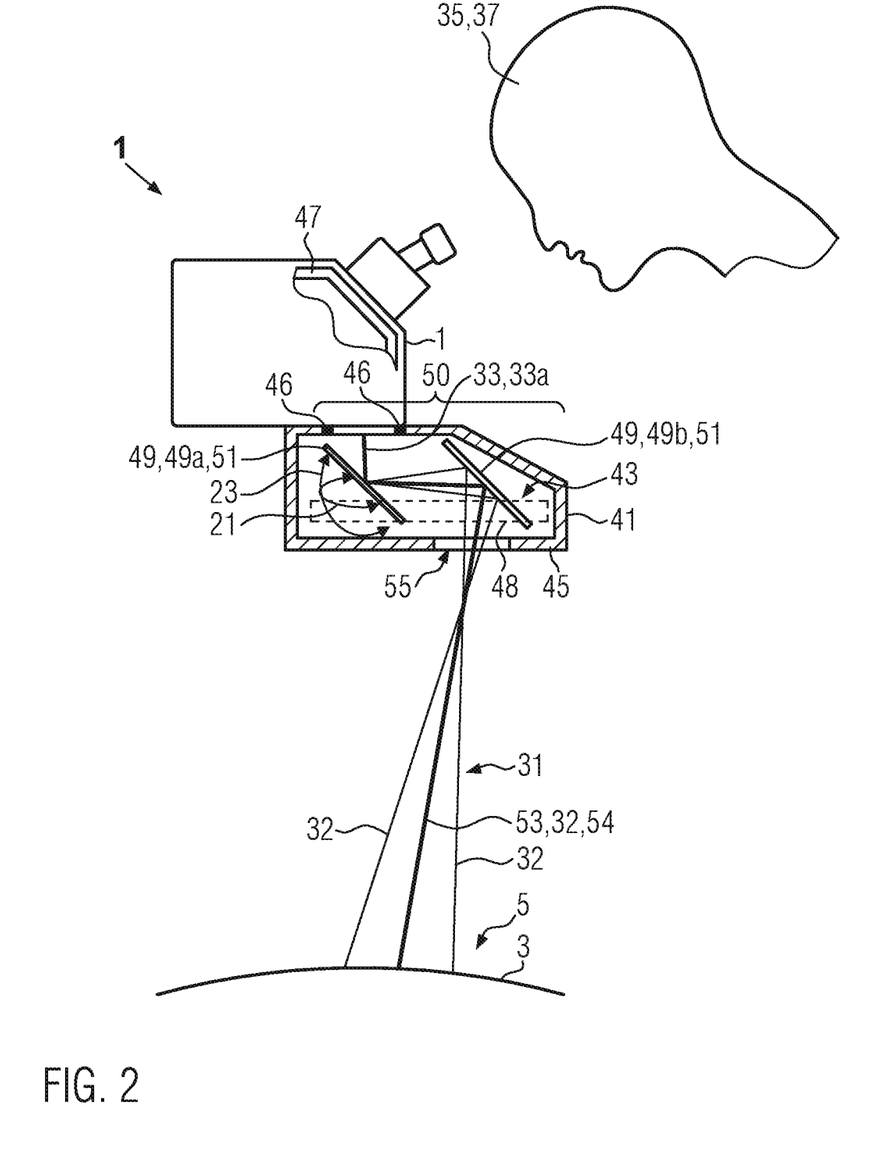
FIG. 2: a surgical microscope of the art with a retrofit-kit according to the invention.

FIG. 2 is a side view of a surgical microscope 1 of the art and a retrofit-kit 41 according to the invention, wherein the retrofit-kit 41 is partially cut, i.e. an interior 43 comprised within a housing 45 is shown. The retrofit-kit 41 is mounted to the surgical microscope 1 by a coupling 46 which is ring-shaped and which may support the at least one beam deflector in another embodiment.

The surgical microscope 1 comprises an optical carrier 47 shown in a partially cut portion. Said optical carrier 47 supports optical elements (not shown) of the surgical microscope 1.

Figure 4:
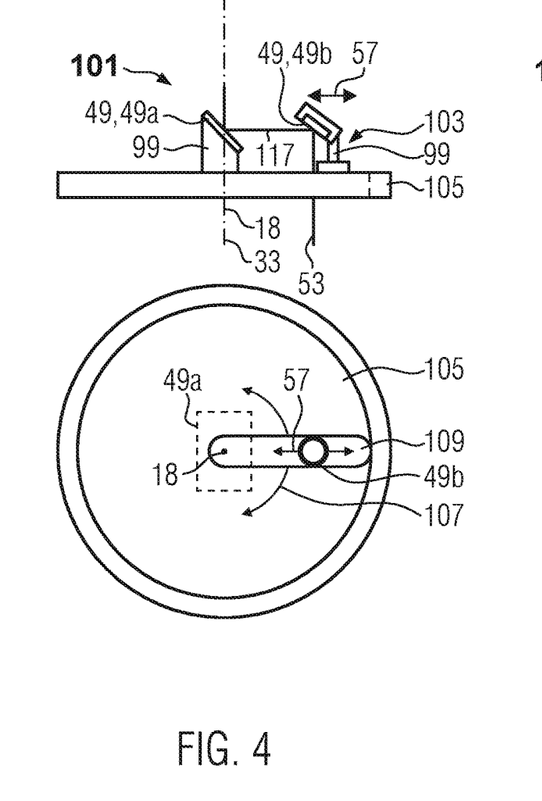
FIG. 4: a first embodiment of an inventive rotational support assembly with a range-setting support assembly.
Figure 5:
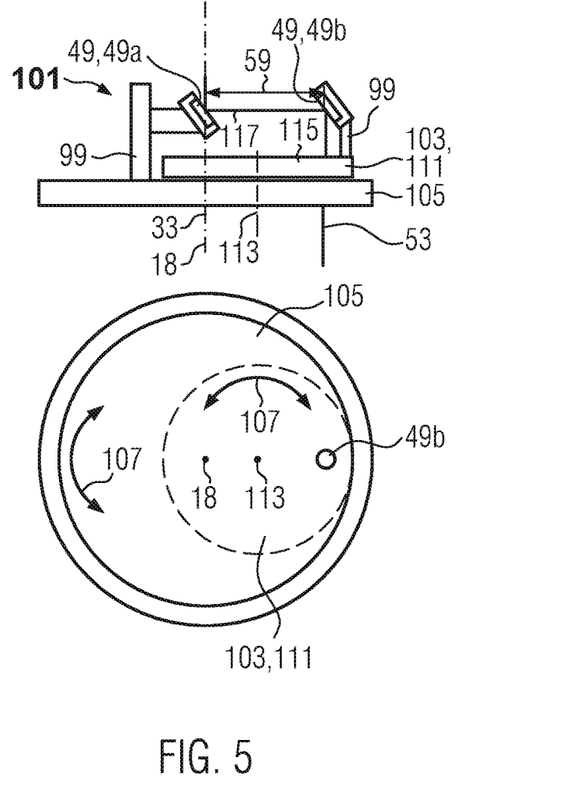
FIG. 5: a second embodiment of the inventive rotational support assembly with a range-setting support assembly.

In the interior 43 of the retrofit-kit, a further optical carrier 48 is schematically indicated with a dashed line, wherein reference is made to FIGS. 4 and 5 in which two specific embodiments of the optical carrier 47 (in case of an inventive surgical microscope; or the further optical carrier 48, if a retrofit-kit 41 is used) are shown.

The further optical carrier 48 comprises two optical beam deflectors 49, i.e. a pair 50 of beam deflectors 49, which are mirrors 51 in the embodiment shown in FIG. 2. In different embodiments of the inventive retrofit-kit 41 the optical beam deflectors 49 may be embodied as refractive elements like prisms or catadioptric elements (not shown). A similar set-up may be provided in an inventive surgical microscope 1 (this specific embodiment is not shown), wherein in such a case at least one of the above-mentioned elements is provided on or at the optical carrier 47.

Instead of tilting the entire surgical microscope 1, a first optical beam deflector 49a may perform the first rotation 21 and the second rotation 23. The third rotation 27 is not envisaged in the embodiment shown but may be provided in another embodiment of the inventive retrofit-kit 41. The surgical microscope 1 therefore remains at a fixed position and there is no need for the surgeon 35 to readjust his or her observation position 37.

Additionally or alternatively, also a second optical beam deflector 49b may be tiltable. The observation axis 33 corresponds to an optical input axis 33a of the retrofit-kit 41. This observation axis 33 is deflected by the optical beam deflectors 49 (or by a single optical beam deflector 49 in another embodiment of the invention) into an optical viewing axis 53 which is directed towards the observation area 5 of the object 3 and which may consequently comprise a variable tilt 31 introduced by the optical beam deflectors 49. Also in FIG. 2, three positions 32 of the optical viewing axis 53 are shown. The optical viewing axis 53 corresponds to an optical output axis 54 of the retrofit-kit 41.

The housing 45 of the retrofit-kit 41 comprises a through-hole 55 which provides access to the at least one optical beam deflector 49 from the observation area 5.

The inventive retrofit-kit 41 of FIG. 2 may be improved by providing a beam combiner and a light source. Those elements are shown in FIG. 3 for the inventive surgical microscope 1.

Figure 3:
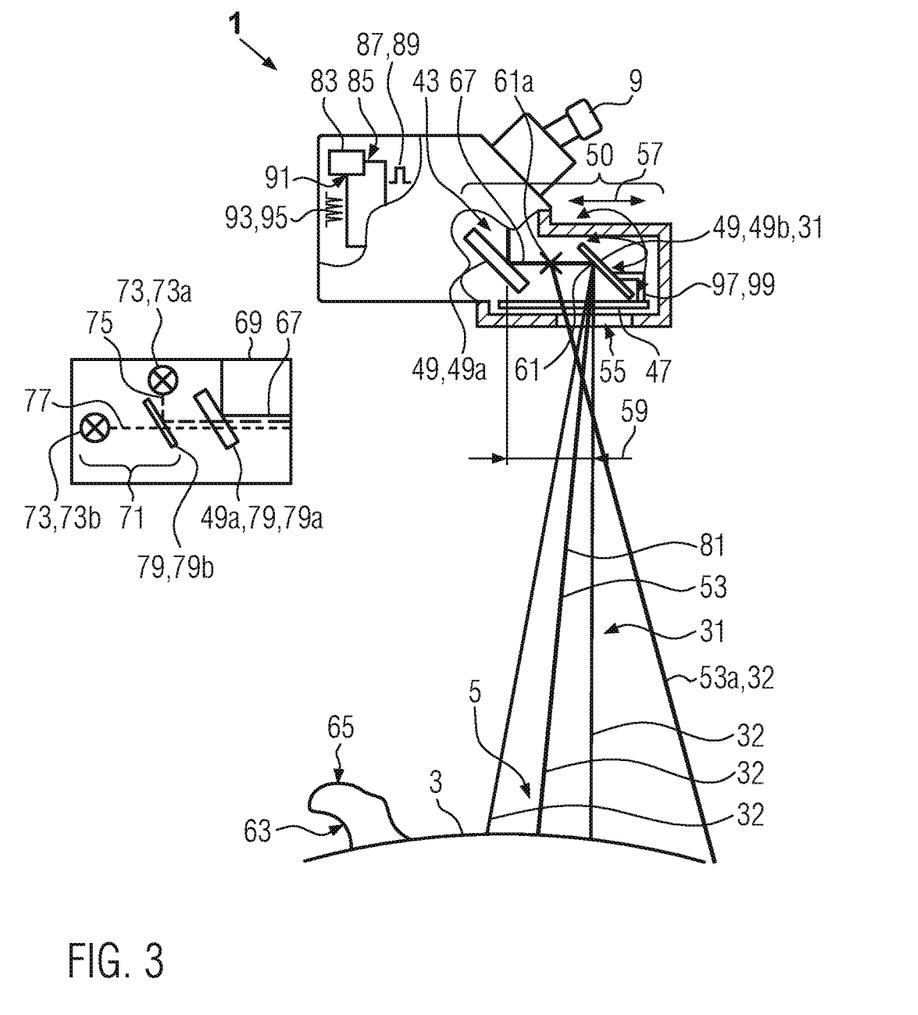
FIG. 3: a first embodiment of the inventive surgical microscope.

FIG. 3 shows a first embodiment of the inventive surgical microscope 1, wherein the schematic drawing is shown partially cut for revealing the interior 43 of the inventive surgical microscope 1. The optical carrier 47, to which the pair 50 of the two optical beam deflectors 49 is attached, is merely indicated.

In comparison to the inventive retrofit-kit 41 shown in FIG. 2, the inventive surgical microscope 1 of FIG. 3 has a fixed first optical beam deflector 49a, wherein the second optical beam deflector 49b is tiltable. Said second optical beam deflector 49b is furthermore movable along a trajectory 57 which indicates a linear movement of the second optical beam deflector 49b with respect to the first optical beam deflector 49a. In other embodiments of the invention, also the first optical beam deflector 49a or both beam deflectors 49 may be movable.

The embodiment shown in FIG. 3 therefore allows changing the tilt 31 of the optical viewing axis 53 as well as a distance 59 between the first optical beam deflector 49a and the second optical beam deflector 49b.

By changing said distance 59, an origin 61 of the optical viewing axis 53 may be relocated for changing the viewing perspective. This is exemplarily indicated by an example origin 61a indicated by a cross, from which example origin 61a and example optical viewing axis 53a may be set by a surgeon 35 (not shown). Thus, FIG. 3 shows four positions 32 of the optical viewing axis 53. Such an oblique example optical viewing axis 53a may, in combination with a repositioning of the object 3, allow for observation of a portion 63 in an undercut area 65. Said portion 63 is exemplarily shown in the figure.

A limitation of the movement of the second optical beam deflector 49b is determined by the tilt 31 of said deflector 49b, by the maximum change of the distance 59 and by the size of the through-hole 55.

The origin 61 is to be understood as the point at which a deflected observation axis 67 is incident on the second optical beam deflector 49b (or on the at least one optical beam deflector 49 if only one such element is applied).

As shown in a rectangle 69 in FIG. 3, the surgical microscope 1 may comprise a light source arrangement 71 which may comprise at least one light source 73. In the rectangle 69 a first light source 73a and a second light source 73b are indicated, wherein any arbitrary number of light sources 73 may be provided. The light sources 73a, 73b may operate in different wavelength ranges and may be pulsed light sources (not shown) or continuous light sources (not shown).

In the embodiment shown in FIG. 3, the first light source 73a emits illumination light 75 which is indicated by a dashed line. The second light source 73b emits excitation light 77 indicated by a dotted line.

The first optical beam deflector 49a is a beam combiner 79, in particular a first beam combiner 79a, which is reflective for observation light 81 propagating from the observation area towards the eyepiece 9. The first beam combiner 79a is in particular reflective for the observation light 81 at a specific, predetermined angle, here approximately 45°. The first beam combiner 79a is furthermore highly transparent for the illumination light 75 and the excitation light 77.

The embodiment of the inventive surgical microscope 1 shown in FIG. 3 furthermore comprises a second beam combiner 79b which is highly transparent for at least the excitation light 77 and reflective for the illumination light 75, in particular at an angle of incidence of approximately 45°.

The arrangement of the first 79a and the second beam combiner 79b allow concurrent overlapping of the illumination light 75 and/or the excitation light 77 with the deflected observation axis 67 (solid line). Only for the sake of visibility, the illumination light 75, the excitation light 77 and the deflected observation axis 67 are drawn spaced apart from each other.

The embodiment of the inventive surgical microscope 1 shown in FIG. 3 furthermore comprises a controller module 83 with at least one control data input terminal 85 for inputting control data 87 which is indicated by a single rectangular pulse 89.

The controller module 83 also comprises at least one driving data output terminal 91 for providing driving data 93 which is indicated by a pulse sequence 95. Said driving data 93 is provided to a drive system 97 which is provided at a post 99 which supports the second optical beam deflector 49b. The drive system 97 allows moving and/or tilting of the at least one optical beam deflector 49, in the embodiment shown the second optical beam deflector 49b is moved and/or tilted. The drive system 97 may thus comprise linear actuators (not shown) and rotational actuators (not shown).

FIGS. 4 and 5 show different embodiments of an inventive rotational support assembly 101 and a range-setting support assembly 103. Both assemblies 101, 103 may be attached to or supported by the optical carrier 47 of the inventive surgical microscope 1 or the further optical carrier 48 of the inventive retrofit-kit 41. The viewing direction of the lower panel of both figures is from the observation area 5 along the optical viewing axis 53 towards the at least one optical beam deflector 49. The upper panel of both figures shows a side view of the inventive rotational support assemblies 125.

In the embodiment of the rotational support assembly 101 shown in FIG. 4, the first optical beam deflector 49a and the second optical beam deflector 49b are attached via posts 99 to a rotation base 105, which may perform a rotation 107 around the rotational axis 18 of the rotational support assembly 101. The rotational axis 18 corresponds to the observation axis 33. A rotation 107 of the rotational support assembly 101 therefore does not change the relative position between the first optical beam deflector 49a and the second optical beam deflector 49b.

This embodiment furthermore comprises the range-setting support assembly 103 which comprises a guiding slot 109, along which the post 99 supporting the second optical beam deflector 49b may be moved following the linear trajectory 57. FIGS. 4 and 5 do not show a drive system 97 for moving and/or tilting of the optical beam deflectors 49.

FIG. 5 shows a further embodiment of the inventive rotational support assembly 101, wherein the range-setting support assembly 103 is embodied as a radial range-setting support system 111. In this embodiment, the first optical beam deflector 49a is supported by the rotation base 105 and rotatable around the rotational axis 18. The radial range-setting support system 111 of this embodiment does not perform a linear movement but a rotation 107 around a support system axis 113 which is essentially parallelly offset from the rotational axis 18.

The second optical beam deflector 49b is supported by a post 99 and attached to a support system base 115 of the radial range-setting support system 111.

The rotational support assembly 101 and the radial range-setting support system 111 may be rotated either independently of each other or in a synchronized manner.

In particular, a combination of the rotation 107 of the rotational support assembly 101 and the (off-center) rotation 107 of the radial range-setting support system 111 may change the distance 59 between the first optical beam deflector 49a and the second optical beam deflector 49b.

In order to maintain an optical path 117 on the first optical beam deflector 49a on the second optical beam deflector 49b, the optical beam deflectors 49 may also be rotatable in themselves, i.e. around a rotational axis through the corresponding beam deflector 49 and in particular relative to the rotational support assembly 101 and/or to the radial range-setting support system 111.

REFERENCE SIGNS 1 surgical microscope
3 object 5 observation area
7 optical observation assembly
9 eyepiece
11 ocular
13 objective assembly
15 gimbal mount
17 joint
18 rotational axis
19 vertical axis
21 first rotation
23 second rotation
25 first horizontal axis
27 third rotation
29 second horizontal axis
31 tilt
32 position
33 observation axis
33a optical input axis
35 surgeon
37 observation position
39 field of view
41 retrofit-kit
43 interior
45 housing
46 coupling
47 optical carrier
48 further optical carrier
49 optical beam deflector
49a first optical beam deflector
49b second optical beam deflector
50 pair
51 mirror
53 optical viewing axis
53a example optical viewing axis
54 optical output axis
55 through-hole
57 trajectory
59 distance
61 origin
61a example origin
63 portion
65 undercut area
67 deflected observation axis
69 angle
71 light source arrangement
73 light source
75 illumination light
77 excitation light
79 beam combiner
79a first beam combiner
79b second beam combiner
81 observation light
83 controller module
85 control data input terminal
87 control data
89 rectangular pulse
91 driving data output terminal
93 driving data
95 pulse sequence
97 drive system
99 port
101 rotational support assembly
103 range-setting support assembly
105 rotational base
107 rotation
109 guiding slot
111 radial range-setting support system
113 support system axis
115 support system base
117 optical path

What is claimed is:

1. A surgical microscope for observing an object in an observation area during surgery, comprising:
an optical observation assembly having an observation axis; and
at least one optical carrier for variably deflecting the observation axis into an optical viewing axis directed towards the observation area, wherein the optical carrier comprises at least one optical beam deflector and is arranged between the optical observation assembly and the observation area;
wherein the optical carrier comprises a moveable range-setting support system for supporting the at least one optical beam deflector of the optical carrier and for positioning the at least one optical beam deflector at a variable distance from the optical observation assembly.

2. The surgical microscope according to claim 1, wherein the at least one optical beam deflector is moveable with respect to the optical observation assembly with regard to at least one of tilt and distance.

3. The surgical microscope according to claim 2, further comprising a drive system for moving and/or tilting the at least one optical beam deflector.

4. The surgical microscope according to claim 3, further comprising a controller module having at least one control data input terminal for inputting control data and having at least one driving data output terminal connected to the drive system for providing driving data to the drive system.

5. The surgical microscope according to claim 1, wherein the optical carrier comprises a pair of optical beam deflectors, wherein at least one of the pair of optical beam deflectors is tiltable and/or moveable with respect to the other of the pair of optical beam deflectors.

6. The surgical microscope according to claim 1, wherein the optical carrier comprises a rotational support assembly for supporting the at least one optical beam deflector of the optical carrier, the rotational support assembly being rotatable around a rotational axis.

7. The surgical microscope according to claim 6, wherein the rotational axis coincides with the observation axis of the optical observation assembly.

8. The surgical microscope according to claim 1, wherein the optical carrier comprises a rotational support assembly for supporting the at least one optical beam deflector of the optical carrier, the rotational support assembly being rotatable around a rotational axis, and wherein the range-setting support system is supported by the rotational support assembly.

9. The surgical microscope according to claim 8, wherein the range-setting support system is a radial range-setting support system which is rotatable around a support system axis, wherein the rotation of the radial range-setting support system is synchronized with the rotation of the rotational support assembly.

10. The surgical microscope according to claim 1, further comprising a light source arrangement for providing illumination light and/or excitation light to the observation area.

11. The surgical microscope according to claim 10, wherein the illumination light and/or the excitation light propagates at least in portions essentially coaxially with the optical viewing axis.

12. The surgical microscope according to claim 1, wherein the range-setting support system comprises a through-hole for providing access to the at least one optical beam deflector from the observation area.

13. A method for observing an object in an observation area during surgery, comprising the steps of:
- variably deflecting an observation axis of an optical observation assembly via at least one optical carrier into an optical viewing axis directed towards the observation area, wherein the optical carrier comprises at least one beam deflector and is arranged between the optical observation assembly and the observation area; and
- propagating light stemming from the observation area essentially along the optical viewing axis and the observation axis and imaging said light via an optical observation assembly;
- wherein the optical carrier comprises a moveable range-setting support system for supporting the at least one optical beam deflector of the optical carrier and for positioning the at least one optical beam deflector at a variable distance from the optical observation assembly.

14. A retrofit-kit for a surgical microscope, comprising at least one coupling with at least one optical beam deflector, and an optical input axis which is variably deflected into an optical output axis by the at least one optical beam deflector, wherein the coupling is adapted to be mounted to a surgical microscope, such that the optical input axis corresponds to the observation axis of an optical observation assembly of the surgical microscope;
- wherein a moveable range-setting support system supports the at least one optical beam deflector and positions the at least one optical beam deflector at a variable distance from the optical observation assembly.

* * * * *